(12) United States Patent
Suthanthiran et al.

(10) Patent No.: US 6,641,811 B1
(45) Date of Patent: Nov. 4, 2003

(54) USE OF ANGIOTENSIN II INHIBITORS TO PREVENT MALIGNANCIES ASSOCIATED WITH IMMUNOSUPPRESSION

(75) Inventors: Manikkam Suthanthiran, Scarsdale, NY (US); Mary Maluccio, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/781,146

(22) Filed: Feb. 9, 2001

Related U.S. Application Data

(60) Provisional application No. 60/181,485, filed on Feb. 10, 2000.

(51) Int. Cl.$^7$ .................... A61K 39/00; A01N 61/00
(52) U.S. Cl. .................. 424/146.1; 424/184.1; 514/1
(58) Field of Search .............. 424/184.1, 277.1; 514/1

(56) References Cited

PUBLICATIONS

Volpert et al. (J.Clin.Invest., 1996, vol. 98, No. 3 pp. 671–679).*
Kim et al., (Drug Chem. Toxicol., 1989, vol. 12(3–4), abstract).*
Hojo et al. (Nature, Feb. 11, 1999, vol. 397, pp. 530–534).*
Wolf et al. (J.Clin.Invest, vol 92, 1993, pp. 1366–1372).*
Paine–Murrieta et al. (Cancer Chemother.Pharmacol, vol. 40, 1997, pp. 209–214).*
Baselga et al. (J.Natl.Canc.Inst., 1993, vol. 85, No. 16, abstract).*
Tschmelitsch et al. (Canc.Res., 1997, vol. 57, No. 11, abstract).*
M. Maluccio, et al., "Angiotensin II Receptor Blockade: A Novel Strategy to Prevent Immunosuppressant–Associated Cancer Progression", Transplantation Proceedings (2001) 33 1820–1821.
Hojo, et al., "Cyclosporine induces cancer progression by a cell–autonomous mechanism", Nature (1999) 397 530–534.
Gary J. Nabel, "A transformed view of cyclosporine", Nature (1999) 397 471–472.
Khanna, et al., "Regulation of new DNA Synthesis in Mammalian Cells by Cyclosporine", Transplantation (1994) 57 577–582.

* cited by examiner

Primary Examiner—Anthony C. Caputa
Assistant Examiner—Gary B. Nickol
(74) Attorney, Agent, or Firm—Hoffmann & Baron, LLP; Irving N. Feit

(57) ABSTRACT

The invention provides a method for reducing formation or progression of neoplasms associated with immunosuppressive therapy in a mammal, the method comprising treating the mammal with an effective amount of an angiotensin II inhibitor. In addition the invention provides a method of preventing or treating a neoplasm in a mammal, the method includes treating the mammal with an effective amount of an angiotensin II inhibitor where the treatment is not associated with chemotherapy or radiation therapy. Also provided are compositions comprising an angiotensin II inhibitor and an immunosuppressive agent such as cyclosporin or FK506. The angiotensin II inhibitor of the invention includes proteins and polypeptides that bind angiotensin II receptors, anti-angiotensin II antibodies, angiotensin II receptors and fragments thereof. In another aspect the invention provides methods for identifying compounds capable of inhibiting the formation or proliferation of tumors in a mammal undergoing immunosuppressive therapy.

15 Claims, No Drawings

USE OF ANGIOTENSIN II INHIBITORS TO PREVENT MALIGNANCIES ASSOCIATED WITH IMMUNOSUPPRESSION

This application claims the benefit of U.S. Provisional Application Ser. No. 60/181,485 filed on Feb.10, 2000.

This work was supported at least in part by a grant award from the National Institutes of Health. The government may have certain rights to this invention.

BACKGROUND

Malignancy is a common and dreaded complication following organ transplantation (References 1–4). The high incidence of neoplasms and its aggressive progression, which are associated with immunosuppressive therapy, has been thought to be due to the resulting impairment of the organ graft recipient's immune surveillance system.

Cyclosporine, a cyclic peptide (also known as cyclosporin A or CsA) and the macrolide FK506 (tacrolimus) are well known and widely used immunosuppressants for transplant recipients and autoimmune patients. Cyclosporine has had major impact on improving patient outcome following organ transplantation (References 4 and 5). Drugs typically employed as immunosuppressive agents include cyclosporine, azathioprine, leflunomide, rapamycin and other FKBP targeted compounds including dexamethasone; also included in this group are steroids (including corticosteroids), antilymphocyte globulins, and monoclonal anti-T cell antibodies.

A surprising mechanism for the heightened malignancy that is independent of host immunity has been discovered. In a co-filed application entitled "Use of TGF-β antagonists to inhibit tumor cell formation or progression" the present inventors, et al., have disclosed that TGF-β antagonists are effective in reducing or eliminating the incidence of neoplasms mentioned above. Herein yet further methods and compositions comprising angiotensin II inhibitors useful for preventing or overcoming these complications are provided.

Angiotensin II is an octapeptide biological signaling molecule produced from the decapeptide precursor, angiotensin I by the action of an enzyme: Angiotensin coverting enzyme (ACE). Angiotensin I itself is produced from the protein angiotensinogen circulating in plasma by the action of the enzyme Renin. These molecules form part of the signaling pathway involved in the homeostatic regulation of blood volume. This regulation of blood pressure is reflected in changes in blood pressure, administration of angiotensin II mediates a wide range of biological changes, including vasoconstriction and a consequent increase in blood pressure. For this reason angiotensin II inhibitors are commonly used clinically to control high blood pressure.

The present invention addresses the need for immunosupressive therapies that confer a lower risk of malignancies associated with treatment.

SUMMARY OF THE INVENTION

The invention provides methods for reducing formation or progression of neoplasms associated with immunosuppressive therapy in a mammal. The methods include treatment of the mammal with an effective amount of an angiotensin II inhibitor.

Also provided are compositions for use in these methods. The compositions comprise an effective amount of an angiotensin II inhibitor and an immunosuppressive agent.

The invention also provides alternative methods of treatment for reducing formation or progression of a neoplasm in a mammal. The method includes treating the mammal with an effective amount of an angiotensin II inhibitor, where the treatment is not part of a chemotherapy regimen or a radiation therapy treatment regimen.

In addition, the invention provides methods for identifying angiotensin II inhibitor compounds capable of inhibiting the formation or proliferation of tumors in a mammal undergoing immuno-suppressive therapy. These methods comprise: first providing a test mammal with a tumor cell; second, treating the test animal with an immunosuppressive agent in an immunosuppressive regimen, followed by administering the angiotensin II inhibitor candidate to the test mammal; third, monitoring the growth of the tumor cell in the test mammal; and then comparing the growth of the tumor cell in the test animal with the growth of a tumor cell in a control animal undergoing an identical immunosuppressive regimen, but which has not been treated with the angiotensin II inhibitor test compound.

DETAILED DESCRIPTION OF THE INVENTION

The invention provides methods for reducing formation or progression of a neoplasm associated with immunosuppressive therapy in a mammal by treating with an angiotensin II inhibitor. "Reducing formation or progression" of a neoplasm as used herein means prevention of initiation, establishment, or inhibition of proliferation or metastasis of the neoplasm.

Neoplasms include all forms of cancer cells and cell masses known as tumors, which may be malignant or benign, and may be invasive or non-invasive. Tumors include solid tumors and disseminated tumors. For example disseminated tumors include lymphomas and leukemias, and the like. Other tumors such as solid tumors include without limitation, adenocarcinomas, carcinomas, myelomas, melanomas, gliomas, sarcomas, adenosarcomas, adenomas and the like.

Tumors can occur in virtually all parts of the human body, including every organ. The tumors may, for example, be present in the breast, heart, lung, small intestine, colon, spleen, kidney, bladder, head and neck, ovary, prostate, brain, pancreas, skin, bone, bone marrow, blood, thymus, uterus, testicles, cervix, and liver. These examples are included for illustrative purposes and are not intended to be limiting in any way.

The neoplasms treatable by the methods of the present invention are associated with the immunosuppressive therapy and may occur at any stage of the therapy. The term associated with the immunosuppressive therapy means these neoplasms may be potentiated, formed, progress, proliferate or metastasise during the immunosuppressive therapy. For example, the neoplasms may be caused or mediated by the immunosuppressive therapy.

The immunosuppressant used for therapy is not a limiting feature of the invention and may be any immunosuppressant which is capable of altering the expression or regulation of TGF-β. Immunosuppressants are currently used in treatment of transplant recipients and autoimmune patients (e.g. those suffering from rheumatoid arthritis, lupus erythematosus, Crohn's disease and inflammatory bowel disease). Such immunosuppresants include cyclosporine; FK506 (for a review, see for example Adler et al. *Curr Opin Nephrol Hypertens* 7(5):539–45 (1998)); azathioprine (reviewed in Gaffney & Scott *Br J Rheumatol* 37(8):824–36 (1998)); Leflunomide (see Prakash & Jarvis *Drugs* 58(6): 1137–64); Rapamycin and analogs (see for example U.S. Pat. Nos.

5,985,890; 5,998,408; 6,015,815 and 6,022,890) or any compound which mimics FK506 in binding to immunophilin (FKBP: see U.S. Pat. No. 5,968,802); steroids, particularly corticosteroids and dexamethasone or any other compounds which stimulate T-cells to produce TGF-β; anti-lymphocyte globulins and monoclonal anti-T cell antibodies, or any other immunosuppressant that induces TGF-β.

The methods comprise treating the mammal with an angiotensin II inhibitor. An angiotensin II inhibitor is any molecule that reduces an effect of angiotensin II by any mechanism.

For example the angiotensin II inhibitor may be an angiotensin II antagonist that inhibits or blocks angiotensin II activity. This may be achieved by any one of a variety of means: For example, the angiotensin II inhibitor may hinder the binding of angiotensin II to the receptor binding site, or it may reduce the signaling by the receptor to its effector molecules, such as the coupled G-proteins in the signal transduction cascade.

Alternatively, the angiotensin II inhibitor may prevent angiotensin II production from its precursor molecule, angiotensin I, as for example when the angiotensin II inhibitor is an angiotensin converting enzyme (ACE) inhibitor. Many peptido-mimetic ACE inhibitors are available and are widely used (see below).

In yet another alternative, the angiotensin II inhibitor may be a compound that inhibits the production of the angiotensin II precursor, angiotensin I from angiotensinogen by inhibiting renin, the enzyme that catalyses this reaction. Renin inhibitors are also available and well known to those of skill in the art.

These effects may be achieved by any one or more of a variety of still other means, e.g. by interfering with the transcription of the angiotensinogen gene, or by interfering with the expression of the angiotensinogen protein from the angiotensinogen mRNA.

The angiotensin II inhibitor in accordance with the methods and compositions of the invention can be any molecule. Two classes of molecules are arbitrarily defined for the purposes of this specification. These two classes are biological molecules and small molecules.

Biological molecules include all lipids and polymers of monosaccharides, amino acids and nucleotides having a molecular weight greater than 450. Thus, biological molecules include, for example, oligosaccharides and polysaccharides, polypeptides, peptides, and proteins; and nucleic acids including oligonucleotides and polynucleotides. Oligonucleotides and polynucleotides include, for example, DNA and RNA. The RNA or DNA molecules may be antisense molecules. Antisense molecules are nucleic acid molecules complementary to the "sense" nucleic acid molecules encoding peptide and protein products.

Biological molecules further include derivatives of any of the molecules described above. For example, derivatives of biological molecules include lipid and glycosylation derivatives of oligopeptides, polypeptides, peptides and proteins. Derivatives of biological molecules further include lipid and glycosylated derivatives of oligosaccharides and polysaccharides, e.g. lipopolysaccharides.

Examples of biological molecules useful for practicing the invention include antibodies, such as polyclonal anti-angiotensin(ogen) antibodies, monoclonal anti- angiotensin (ogen) antibodies, fragments of these antibodies which comprise the antigen binding regions and single chain antibodies.

As used herein, the term antibody refers to an intact antibody as well as antigen-binding fragments of the intact antibody. Antigen-binding fragments of the intact antibody include (but are not limited to) F(ab)$_2$ fragments, Fv fragments, single chain antibodies and other antibody fragments comprising the angiotensin II-binding site.

Biological molecules also include angiotensin II receptors, whether natural or recombinant. Also included are angiotensin II receptor fragments that retain the ability to bind angiotensin II, and soluble forms of angiotensin II receptor fragments that retain angiotensin II-binding properties.

Any molecule that is not a biological molecule is considered in this specification to be a small molecule. Accordingly, small molecules include organic compounds, inorganic compounds, organometallic compounds, salts of organic and organometallic compounds, saccharides, amino acids, and nucleotides. Small molecules further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

An example of biological molecules which are angiotensin II inhibitors according to the present invention are the anti-renin monoclonal antibodies of U.S. Pat. No. 4,780,401.

It is emphasized that small molecules can have any molecular weight. They are merely called small molecules because they typically have molecular weights less than 450. Small molecules include compounds that are found in nature as well as synthetic compounds.

Thus, all molecules are intended to be covered by one or the other of the above definitions. For example, the molecule may comprise a biological molecule bonded to a small molecule.

Examples of small molecule angiotensin II antagonists which may be applied to the present invention include, but are not limited to such drugs and drug candidate molecules as Losartan (DuPont's DUP753/MK954) and polymorphs of Losartan are disclosed in U.S. Pat. No. 5,608,075; Saralasin, ES-8891 and related N-substituted imidazole-2-ones (U.S. Pat. No. 5,087,634); SK&F 108566 (SmithKline & French), Remikirin (Roche RO 42–5892); Benzimidazole derivatives as disclosed in U.S. Pat. No. 6,004,989; Ortho-substituted benzoylguanidines U.S. Pat. No. 6,001,881; Also small molecule angiotensin II antagonists which are angiotensin II receptor antagonists may be applied to the present invention. Examples of such angiotensin II antagonists include those disclosed in U.S. Pat. No. 5,958,884 and 5,264,581; and other angiotensin II receptor type AT1 and AT2 blockers as disclosed in U.S. Pat. No. 5,889,020.

Examples of small molecule angiotensin II antagonists which are ACE inhibitors useful for the practice of the present invention are BRL 36,378 of Beecham Laboratories disclosed in EP80822 and EP60668; CGS 14824 disclosed in UK Patent No. 2103614 and CGS 16,617 disclosed in U.S. Pat. No. 4,473,575 of Ciba Geigy; MC-838 of Chugai Pharmaceuticals disclosed in Canadian Patent No. 102:72588v; the mercaptoalkanoyl prolines such as Captopril (U.S. Pat. No. 4,105,776) and Zefenopril (U.S. Pat. No. 4,316,906); the carboxyalkyl dipeptide derivatives such as Enalapril (U.S. Pat. No. 4,374,829), Quinapril (U.S. Pat. 4,344,949), Perindopril (U.S. Pat. No. 4,508,729), Ramipril (U.S. Pat. No. 4,587,256) and Lisinopril (U.S. Pat. No. 5,045,553); and the carboxyalkyl dipeptide mimics such as Benzazepril (U.S. Pat. No. 4,410,520) and Cilazapril (U.S. Pat. No. 4,512,924).

Further examples of small molecule angiotensin II antagonists which are ACE inhibitors useful for the practice of the present invention include the phosphoalkanoyl prolines such as Fosinopril (U.S. Pat. No. 4,168,267) and Fisinopril (U.S. Pat. No. 4,337,201), the phosphinylalkanoyl prolines such as Trandopril and Pamipril (U.S. Pat. No. 5,256,687), the ether/thioether mercaptoacyl prolines such as Zefenopril (U.S. Pat. No. 4,316,906), the N-aminoacyl amino acid derivatives such as Anapryl (U.S. Pat. No. 5,589,499), the phosphonate substituted amino/imino acids such as Ceranopril (U.S. Pat. No. 4,452,790) and the phosphoamidates (See U.S. Pat. No. 4,432,971).

Examples of small molecule angiotensin II antagonists which are renin inhibitors applicable to the present invention are urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tripeptide derivatives (U.S. Pat. No. 5,106,835), peptidyl amino diols(U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos: 5,071,837; 5,064,965; 5,063,207; 5,036,054; 5,036,053; 5,034,512 and 4,894,437.

Further examples of small molecule angiotensin II antagonists which are renin inhibitors which may be applied to the present invention include diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statonecontaining peptides (U.S. Pat. No. 5,066,643).

Furthermore, anti-renin monoclonal antibodies such as those disclosed in U.S. Pat. No. 4,780,401 may be utilized as angiotensin II antagonists in the methods of the present invention.

The angiotensin II inhibitor may be administered at any time relative to the immuno-suppressive therapy. For example, the methods of the invention include pretreatment with a angiotensin II inhibitor. Alternatively, the angiotensin II inhibitor may be administered contemporaneously with immunosuppressive therapy. Another method of administration of the angiotensin II inhibitor is after immunosuppressive therapy. Any combination of the above mentioned regimens may be used, resulting in overlapping treatment. The immunosuppressant used for therapy may be cyclosporine, FK506 or any other immunosuppressant which directly or indirectly induces angiotensin II.

As used herein an "effective amount" of an angiotensin II inhibitor is any amount that detectably reduces the formation or progression of a neoplasm that is associated with immunosuppressive therapy.

For the purposes of the present specification, the term "reduction of the formation or progression of neoplasms" shall include the detectable inhibition of establishment, growth, progression or metastasis of the neoplasm and also includes the reduction in size of a tumor or other neoplastic tissue. A quantitative measure of the amount of reduction of the incidence of neoplasms in a population of treated subjects as compared with a placebo population may be determined in a pre-clinical or a clinical trial. These trials are typically performed as part of the government approval and licensing procedure for a drug candidate that is a new chemical entity.

For example, the establishment, growth or progression of neoplasms may be reduced by at least about 10%, preferably the establishment, growth, progression or metastasis of neoplasms may be reduced by at least about 25%, more preferably by at least about 50% and still more preferably by at least about 75%. Yet more preferably the establishment, growth, progression or metastasis of neoplasms may be reduced by at least about 90% and more preferably still the establishment, growth, progression or metastasis may be reduced by at least about 99%. Optimally, the establishment, growth, progression or metastasis of neoplasms may be reduced by 100%, i.e. completely inhibited. For instance, complete inhibition of the establishment, growth or progression or metastasis of neoplasms may be achieved in the methods of the present invention using a neutralizing antagonist, an example of such a neutralizing antagonist may for instance, be a neutralizing antibody.

Inhibition of growth or progression of neoplasms may be assessed qualitatively or quantitatively. Inhibition of proliferation may be assessed qualitatively as a detectable change in growth or proliferation. Alternatively, inhibition of proliferation may be assessed quantitatively where the detectable change is the difference between a measured proliferation parameter in the test cell contacted with the test compound and in an identical control untreated cell. An example of such a proliferation parameter is the incorporation of $^3$H-thymidine from H-TTP into chromosomal DNA.

The effective amount of an angiotensin II inhibitor can be routinely determined by a person of ordinary skill in the art. For example, an effective amount of compound per weight of cells or body weight may be between 1 and 100 ng/kg, but is preferably between 1 and 100 ug/kg, or between 1 and 100 mg/k, but may also be 1 gm/kg or even 10 gm/kg body weight. The effective amount may be administered once, twice, three times or four times per day, or alternatively, every 4 hrs or every 6 hrs.

Administering an effective amount of the compound in a pharmaceutically acceptable carrier may be achieved by a variety of routes, including for example, intravenously (i.v.), subcutaneously, interperitoneally (i.p.), topically, alone or in combination with other medicinal compounds, or in some embodiments the compound may be administered orally (p.o.) as with solid food or liquids, syrups etc.

The method of the present invention is applicable to any mammal. Examples of mammals to which the method may be usefully applied include laboratory animals, including rodents such as mice, rats and guinea pigs; farm animals such as cows, sheep, pigs and goats; pet animals such as dogs and cats; and primates such as monkeys, apes and humans, i.e. patients. The invention is most preferably applied in human clinical situations.

In one embodiment, the method is particularly useful where the patient is undergoing immunosuppressive therapy after organ or tissue transplantation, or any other form of surgery where suppression of the immune system of the patient is indicated. However, other mammals may also benefit from the practice of the invention. These other high value animals such as horses and fur animals such as mink.

These therapeutic methods of the present invention may be combined with traditional cancer treatments. Treatments of cancer traditionally include chemotherapy or radiation therapy.

Some examples of chemotherapeutic agents include doxorubicin, cisplatin, and taxol. The radiation can be either from an external beam or from a source placed inside a patient, i.e., brachytherapy.

The compositions of the present invention comprising angiotensin II inhibitor and an immunosuppressive agent are preferably formulated in a pharmaceutically acceptable carrier.

The compositions, may be delivered by parenteral injection or may be delivered orally, for example in mixtures comprising approved carriers, (generally accepted as safe for use in foods).

In another embodiment, the method is particularly useful where the patient is in need of treatment or prevention of a neoplasm. The method includes treating the mammal with an effective amount of an angiotensin II inhibitor, where the treatment is not part of a chemotherapy or radiation therapy treatment regimen.

In another embodiment the invention provides a method for screening for anti-cancer drugs. The screening method of the present invention provides a method of identifying compounds capable of inhibiting the formation or proliferation of tumors in a mammal undergoing immunosuppressive therapy. The method comprises: first providing a test mammal with a tumor cell; second treating the test mammal with an immunosuppressive agent in an immunosuppressive regimen; third administering the test compound to the test mammal; then monitoring the growth of the tumor cell in the test mammal; and finally, comparing the growth of the tumor cell in the test mammal with the growth of the tumor cell inoculated into a control animal. In a particular embodiment, the test compound is an angiotensin II inhibitor.

The test mammal may be any mammal particularly a laboratory animal. Such animals may be rats or mice, and preferably the animals are immune deficient animals. SCID/SCID and SCID-beige mice are particularly well suited for this method. The tumor cells may be any tumor cells, particularly murine cells e.g. renca cells (renal adenocarcinoma cells); Lewis Lung carcinoma cells; mammary gland epithelial cells (e.g. NmuMG cells); mink lung epithelial cells (e.g. CCL-64 cells). Human tumor cells are particularly preferred, including for instance, human bladder transitional carcinoma cell (HTB, human lung adenocarcinoma cells such as A-549 cells, and human bladder cancer cell lines such as T24 cells).

In a particularly advantageous embodiment the screening method of the present invention the test animal is a SCID-beige mouse and the tumor cells is a tumor cell selected from the following: renca cells (renal adenocarcinoma cells); Lewis Lung carcinoma cells; mammary gland epithelial cells (e.g. NmuMG cells); mink lung epithelial cells (e.g. CCL-64 cells). Human tumor cells are particularly preferred, especially one of the following: human bladder transitional carcinoma cells (HTB, human lung adenocarcinoma cells such as A-549 cells, and human bladder cancer cell lines such as T24 cells). In the preferred embodiment the growth of the tumor cells that is monitored is anchorage-independent growth.

The specifications of the following U.S. Patents reflect the state of the art and may be useful in practicing the full scope of the present invention. The specifications of these U.S. patents cited below are hereby incorporated by reference.

U.S. Pat. No. 5,972,990 is entitled "Methods of reducing risk of repeat myocardial infarction and increasing survival in heart attack victims." U.S. Pat. No. 5,958,884 discloses the use inhibitors and agonists of angiotensin II. U.S. Pat. No. 5,879,889 is entitled "Cancer drug screen based on cell cycle uncoupling." U.S. Pat. No. 5,739,110 is entitled "Protection of hematopoietic cells." U.S. Pat. No. 5,686,451 is entitled "Combination of an ACE inhibitor and a diuretic."

U.S. Pat. No. 5,589,499 is entitled "Dopaminergic agents for the treatment of cerebral and peripheral blood flow disorders." U.S. Pat. No. 5,256,687 is entitled "Pharmaceutical composition for the treatment of high blood pressure." U.S. Pat. No. 5,212,165 is entitled "Method for rehabilitating the vasorelaxant action of the coronary arteries impaired through atherosclerosis or hypercholesterolemia employing an ACE inhibitor." U.S. Pat. No. 5,192,524 is entitled "Captopril as a cancer chemopreventive agent." U.S. Pat. No. 5,049,553 is entitled "Method for preventing or treating symptoms resulting from closed head injuries employing an ACE inhibitor."

In one embodiment, as described above, the present invention provides a method of treatment for reducing formation or progression of a neoplasm in a mammal, particularly a human (patient), the method includes treating the mammal with an effective amount of an angiotensin II inhibitor, where the treatment is not part of a chemotherapy or radiation therapy treatment regimen. These regimens involves the use of either chemotherapeutic agents, or radiation exposure.

Examples of chemotherapeutic agents include alkylating agents, for example, nitrogen mustards, ethyleneimine compounds and alkyl sulphonates; antimetabolites, for example, folic acid, purine or pyrimidine antagonists; mitotic inhibitors, for example, vinca alkaloids and derivatives of podophyllotoxin; cytotoxic antibiotics; and compounds that damage or interfere with DNA expression.

Particular examples of chemotherapeutic agents or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

The administration of small molecule drugs and biological drugs to humans (patients) is accomplished by methods that are well known in the art. For small molecule drugs, such methods are described in Spada, U.S. Pat. No. 5,646,153 at column 57, line 47 to column 59, line 67. This description of administering small molecules is incorporated herein by reference.

Administering chemotherapeutic agents can be accomplished in a variety of ways including systemically by the parenteral and enteral routes, as described above.

The disclosures of all of the patents and other documents cited above reflect the state of the art and may be useful in practicing the full scope of the present invention. All are hereby incorporated by reference.

General Methods

Antibody preparation. Antibodies include polyclonal, monoclonal and recombinant antibodies, including single chain antibodies and antigen-binding fragments of each. Antibodies may be prepared by a wide variety of techniques ranging from techniques including in vivo inoculation, isolation of hybridomas, xenograft techniques, selection or screening based on phage display and many others well known to those of skill in the art. For example, fragments such as Fab fragments may be prepared in accordance with the method of Huse et al., Science 246, 1275–1281 (1989) and Coligan, J. E. et al. (Eds.) Current Protocols in Immunology, Wiley Intersciences, N.Y., (1999).

The antibodies are preferably monoclonal. Monoclonal antibodies may be produced by methods known in the art. These methods include the immunological method described by Kohler and Milstein in Nature 256:495–497 (1975) and by Campbell in "Monoclonal Antibody Technology, The Production and Characterization of Rodent and Human Hybridomas" in Burdon et al. (Eds.), Laboratory Techniques in Biochemistry and Molecular Biology, Volume 13, Elsevier Science Publishers, Amsterdam (1985); and Coligan, J. E, et al. (Eds.), Current Protocols in Immunology, Wiley Intersciences, N.Y., (1999); as well as the recombinant DNA method described by Huse et al., Science 246:1275–1281 (1989).

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256:495–497 (1975). See also Campbell, "Monoclonal Antibody Technology, The Production and Characterization of Rodent and Human Hybridomas" in Burdon et al. (Eds.), Laboratory Techniques in Biochemistry and Molecular Biology, Volume 13, Elsevier Science Publishers, Amsterdam (1985) and Coligan, J. E., et al. (Eds.), Current Protocols in Immunology, Wiley Intersciences, New York, (1999)). These examples are provided for illustration purposes and should not be construed as limiting in any way. Many other methods are equally applicable and those of skill in the art will recognize that a wide variety of other methods that may be used in the present invention.

Preparation of Peptides, Polypeptides and Proteins. Peptides, polypeptides and proteins may be prepared by many different techniques well known to all those of skill in the art. For example, the peptides, polypeptides and even some proteins may be chemically synthesized. Alternatively, the peptides, polypeptides or proteins may be prepared as recombinant molecules or purified from natural sources by methods well known in the art. For example, recombinant form of a protein such as a receptor protein may be prepared by providing DNA that encodes the protein; amplifying or cloning the DNA in a suitable host; expressing the DNA in a suitable host; and harvesting the protein. See inter alia Sambrook, J. et al. (eds), Molecular Cloning, Second Edition, Cold Spring Harbor Laboratory Press, Cold Spring Harbor, N.Y. (1989) and Ausubel, F. M. et al. (eds), Current Protocols in Molecular Biology, John Wiley & Sons, N.Y. (1999). Again these examples are for illustration and are not to be taken as limiting the scope of the invention.

EXAMPLES

Cell lines and cell culture. Human lung adenocarcinoma cells, A-549 cells (ATCC CCL 185, American Type Culture Collection, Rockville, Md.), human bladder transitional cell carcinoma cells (ATCC HTB4, T24), mink lung epithelial cells, CCL-64 (ATCC), mouse mammary gland epithelial cells, NMUMG (ATCC), Lewis lung carcinoma cells (ATCC), were grown in minimum essential medium (MEM) supplemented with 10% fetal bovine serum, at 37° C. in a 95% air-5% $CO_2$ atmosphere. Murine renal adenocarcinoma cells, Renca cells (a gift from Dr. R. H. Wiltrout, National Cancer Institute, Bethesda Md.), were maintained by in vivo serial passages in syngeneic Balb/c mice, as described in reference 6.

Cell proliferation assays. For assaying anchorage-dependent growth, A-549 cells were grown at a density of $2\times10^4$ cells/well in 12-well plates in the presence or absence of CsA. At the end of 96 h treatment, each well received 2 $\mu$Ci of methyl-3H-thymidine, and cells were incubated for an additional 4 h. Cells were washed twice with ice-cold PBS, and fixed with methanol for 60 min. After washing, the fixed cells were lysed with 0.2M NaOH and treated with cold 10% TCA for 15–20 min on ice. The radio-activity, recovered as cold TCA insoluble precipitates, was used for measuring relative cell proliferation by comparing the radioactivity between control and experiment. For an anchorage-independent cell growth, cells spread well on agarose gel were counted using a phase-contrast microscope.

In vivo tumor growth. Murine renal cell adenocarinoma cells ($1\times10^5$ in Hanks balanced salt solution), murine Lewis lung carcinoma cells ($1\times10^5$ cells), or human bladder cancer cells ($1\times10^5$ cells) are injected via the tail vein into 6-wk old male SCID-beige mice. CsA (20 mg/kg in 0.2 ml olive oil) is administered every other day starting from day −1, to day 19 or 23 with respect to tumor inoculation. On day 19 or 23 post tumor inoculation, mice are killed and the number of pulmonary metastases is determined 30 days following endotracheal insufflation of lungs with 15% India ink solution and bleaching the harvested lungs in Fekete's solution. The effect of angiotensin II inhibitors and anti-angiotensin II mAbs and the control $IgG_1$ mAbs on CsA-induced increase in the number of pulmonary metastases is determined by intraperitoneal administration of 200 $\mu$g of mAbs, on a daily basis starting from day −1 to day 19 post tumor inoculation.

EXAMPLE 1

The Angiotensin II blocker, Losartan reduces pulmonary metastasis in SCID-beige mice.

SCID-beige (immunodeficient) mice were inoculated with human bladder cancer cells (T24) or murine renal cancer cells (Renca). Tumor bearing mice were then treated with cyclosporin A or the angiotensin II receptor blocker, losartan or both.

Results are shown in Table 1.

TABLE I

| SCID-beige Treatment | T24 | Renca |
|---|---|---|
| | Number of Pulmonary Metastases (Mean ± SEM) | |
| None | 25 ± 7 | 125 ± 22 |
| CsA (20 mg/kg, SQ, QOD) | 58 ± 11 | 199 ± 40 |
| Losartan (10 mg/kg, SQ, BID) | 12 ± 3 | 67 ± 15 |
| CsA + Losartan | 16 ± 4 | 120 ± 11 | p = one way ANOVA;
T24: p = 0.002;
Renca: p = 0.03

Tumor cells ($1\times10^5$ in HBSS) were injected via the tail vein into SCID-beige mice. CsA (20 mg/kg) was administered every other day from day −1 to day of sacrifice. The mice were sacrificed on day 19 (Renca) and day 23 (T24) and the number of metastases was counted as described (reference 7).

EXAMPLE 2

The ACE inhibitor, Enalapril prevents the development of pulmonary metastasis.

In other experiments FK506 (4 mg/kg) enhanced tumor progression and enalapril, an angiotensin converting enzyme (ACE) inhibitor prevented the development of pulmonary metastasis in experimental animals.

EXAMPLE 3

Enalapril reduces human T-24 bladder pulmonary metastases in SCID beige mice
T-24
Number of metastases* (mean ± SEM)

| Treatment | Enalapril without | Enalapril with | P** |
|---|---|---|---|
| none | 38 ± 4 | 21 ± 3 | 0.01 |
| Cyclosporine | 96 ± 5 | 35 ± 5 | 0.001 |
| FK506 | 72 ± 21 | 30 ± 2 | 0.01 |

*100,000 T-24 human bladder cancer cells were administered by tail vein to generate pulmonary metastases. Cyclosporine (20 mg/kg) or FK506 (4 mg/kg) was administered every other day from day −1 to day of sacrifice, and enalapril (10 mg/kg), intraperitoneal route, was administered twice a day.
**P value by t test The data shown in Example 1 at Table I demonstrate that the Angiotensin II inhibitor, losartan reduces the incidence of tumors as compared to controls. This effect is seen in the absence of immunosuppressive agent (CsA or FK506).

Similarly, the data shown in Example 3 demonstrate that the Angiotensin II inhibitor, enalapril reduces the incidence of tumors as compared to controls. This effect is seen in the absence of immunosuppressive agent (CsA or FK506).

This provides a method of treatment for reducing formation or progression of a neoplasm in a mammal, the method comprising treating the mammal with an effective amount of an angiotensin II inhibitor (such as for instance, losartan or enalapril) wherein the treatment is not part of an immunosuppressive therapy regimen, or a chemotherapy or radiation therapy treatment regimen.

References

1. Penn I. Cancers following cyclosporine therapy. Transplantation 43, 32–5 (1987)
2. Yokoyama I, Carr B, Saitsu H, Iwatsuki S, Starzl TE. Accelerated growth rates of recurrent hepatocellular carcinoma after liver transplantation. Cancer 68, 2095–2100 (1991)
3. London N.J., Farmerry S M, Will E J, Davison A M, Lodge J P A. Risk of neoplasia in renal transplant patients. Lancet 346, 403–406 (1995)
4. Suthanthiran M, Strom T B. Renal transplantation. N Engl J Med 331, 365–376 (1994)
5. Kahan B D. Cyclosporine N EngI J Med 321, 1725–1738 (1989)
6. Murphy G P, Hrushesky W J. A murine renal cell carcinoma. J Natl Cancer Inst 50, 1013–1025 (1973)
7. Asano T, Khanna A, Lagman M, Li B, Suthanthiran M. Immunostimulatory therapy with anti-CD3 monoclonal antibodies and recombinant interleukin-2: Heightened in vivo expression of mRNA encoding cytotoxic attack molecules and immunoregulatory cytokines and regression of murine renal cell carcinoma. J Urol 157, 2396–2401 (1997)

What is claimed is:

1. A method for reducing formation or progression of a neoplasm in conjunction with immunosuppressive therapy in a mammal in need thereof, the method comprising treating the mammal with an effective amount of an angiotensin II receptor blocker.

2. The method according to claim 1, wherein the mammal is a human.

3. The method according to claim 1, wherein the immunosuppressive therapy comprises treatment with cyclosporine.

4. The method according to claim 1, in combination with cancer therapy.

5. A method according to claim 1, wherein the angiotensin II receptor blocked is a small molecule.

6. A method for reducing metastasis of a neoplasm in conjunction with immunosuppressive therapy in a mammal in need thereof, the method comprising treating the mammal with an effective amount of an angiotensin II receptor blocker.

7. The method according to claim 6, wherein the mammal is a human.

8. The method according to claim 6, wherein the immunosuppressive therapy comprises treatment with cyclosporine.

9. The method according to claim 6, in combination with cancer therapy.

10. A method according to claim 6, wherein the angiotensin II receptor blocker is a small molecule.

11. A method according to claim 4, wherein the cancer therapy comprises chemotherapy.

12. A method according to claim 11, wherein the chemotherapy comprises treatment with an alkylating agent, an anti metabolite, a mitotic inhibitor, a cytotoxic antibiotic, a compound that damages DNA or a compound that interferes with DNA expression.

13. A method according to claim 12, wherein the chemotherapy comprises treatment with doxorubicin, cisplatin or taxol.

14. A method according to claim 4, wherein the cancer therapy comprises radiotherapy.

15. A method according to claim 14, wherein radiotherapy comprises brachytherapy.

\* \* \* \* \*

UNITED STATES PATENT AND TRADEMARK OFFICE
CERTIFICATE OF CORRECTION

PATENT NO. : 6,641,811 B1
DATED : February 20, 2004
INVENTOR(S) : Suthanthiran et al.

It is certified that error appears in the above-identified patent and that said Letters Patent is hereby corrected as shown below:

Column 6,
Line 27, now reads "$^3$H-thymidine from H-TTP…", and should read -- $^3$H-thymidine from $^3$H-TTP … --

Signed and Sealed this

Thirteenth Day of April, 2004

JON W. DUDAS
*Acting Director of the United States Patent and Trademark Office*